US00PP15345P2

(12) United States Plant Patent
Westhoff

(10) Patent No.: US PP15,345 P2
(45) Date of Patent: Nov. 23, 2004

(54) *CALIBRACHOA* PLANT NAMED 'WESCAICE'

(50) Latin Name: ***Calibrachoa* sp.**
Varietal Denomination: Wescaice

(75) Inventor: Heinrich Westhoff, Südlohn (DE)

(73) Assignee: Josef & Heinrich Westhoff Gartenbau-Spezialkulturen, Südlohn (DE)

( * ) Notice: Subject to any disclaimer, the term of this patent is extended or adjusted under 35 U.S.C. 154(b) by 0 days.

(21) Appl. No.: 10/783,350

(22) Filed: Feb. 21, 2004

(51) Int. Cl.[7] ..... A01H 5/00
(52) U.S. Cl. ..... Plt./263
(58) Field of Search ..... Plt./263

*Primary Examiner*—Kent Bell
*Assistant Examiner*—S B McCormick-Ewoldt
(74) *Attorney, Agent, or Firm*—C. A. Whealy

(57) ABSTRACT

A new and distinct cultivar of *Calibrachoa* plant named 'Wescaice', characterized by its cascading, roughly spherical plant habit; plant branches with tightly spaced internodes; large ovate-shaped leaves; freely flowering habit; uniform flower size; and flowers that are light blue in color.

1 Drawing Sheet

Botanical classification/cultivar designation: *Calibrachoa* sp. cultivar Wescaice.

BACKGROUND OF THE INVENTION

The present Invention relates to a new and distinct cultivar of *Calibrachoa* plant, botanically known as *Calibrachoa* sp., and hereinafter referred to by the name 'Wescaice'.

The new *Calibrachoa* is a product of a planned breeding program conducted by the Inventor in Südlohn, Germany. The objective of the program is to create new *Calibrachoa* cultivars with compact and cascading growth habit, freely branching habit and attractive flower colors.

The new *Calibrachoa* originated from a cross-pollination made by the Inventor during 2000 of a proprietary selection of *Calibrachoa* identified as code number 00P108, not patented, as the female, or seed, parent with a proprietary selection of *Calibrachoa* identified as code number 00P150, not patented, as the male, or pollen, parent. The new *Calibrachoa* was selected by the Inventor in 2000 in a controlled environment in Südlohn, Germany from within the progeny resulting from the cross-pollination.

Asexual reproduction of the new cultivar by terminal cuttings taken in a controlled environment in Südlohn, Germany since 2000, has shown that the unique features of this new *Calibrachoa* are stable and reproduced true to type in successive generations.

SUMMARY OF THE INVENTION

Plants of the cultivar Wescaice have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Wescaice'. These characteristics in combination distinguish 'Wescaice' as a new and distinct cultivar of *Calibrachoa*:

1. Cascading, roughly spherical plant habit.
2. Branches with tightly spaced internodes.
3. Large ovate-shaped leaves.
4. Freely flowering habit.

5. Uniform flower size.
6. Flowers that are light blue in color.

Plants of the new *Calibrachoa* produce flowers that are more open in shape and different in color than plants of the female parent. Also, plants of the new *Calibrachoa* have flowers that remain open under low light levels. Plants of the new *Calibrachoa* have flowers that are a different color than plants of the male parent. Plants of the new *Calibrachoa* also have thicker branches and larger leaves than plants of the male parent.

Plants of the cultivar Wescaice can be compared to plants of the *Calibrachoa* cultivar Wesviolet, disclosed in U.S. Plant Pat. No. 12,584. However in side-by-side comparisons conducted in Südlohn, Germany, plants of the new *Calibrachoa* and the cultivar Wesviolet, differed in the following characteristics:

1. Plants of the new *Calibrachoa* had larger and more rounded leaves than plants of the cultivar Wesviolet.
2. Plants of the new *Calibrachoa* had wider sepals and longer peduncles than plants of the cultivar Wesviolet.
3. Plants of the new *Calibrachoa* produced larger flowers than plants of the cultivar Wesviolet.
4. Plants of the new *Calibrachoa* and the cultivar Wesviolet differed in flower color.

Plants of the cultivar Wescaice can also be compared to plants of the *Calibrachoa* cultivar Carillon Blue, not patented. However in side-by-side comparisons conducted in Südlohn, Germany, plants of the new *Calibrachoa* and the cultivar Carillon Blue, differed in the following characteristics:

1. Plants of the new *Calibrachoa* had more rounded leaves than plants of the cultivar Carillon Blue.
2. Plants of the new *Calibrachoa* had shorter internodes than plants of the cultivar Carillon Blue.
3. Plants of the new *Calibrachoa* produced larger flowers than plants of the cultivar Carillon Blue.
4. Plants of the new *Calibrachoa* and the cultivar Carillon Blue differed in flower color.
5. Plants of the new *Calibrachoa* had broader sepals than plants of the cultivar Carillon Blue.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a close-up view of representative flowers of 'Wescaice'.

The photograph at the bottom of the sheet comprises a side perspective view of typical plants of 'Wescaice' grown in a hanging basket container.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and following description were grown under conditions that closely approximate commercial production conditions during the spring and summer in Südlohn, Germany in a glass-covered greenhouse. Plants were about 20 weeks old from planting rooted cuttings. During the production period, day temperatures ranged from 20 to 25° C., night temperatures ranged from 16 to 18° C. and light levels ranged from 3,000 to 50,000 lux. Plants grown in 12-cm containers were used for the following description.

Botanical classification: *Calibrachoa* sp. cultivar Wescaice.

Parentage:

*Female, or seed, parent.*—Proprietary selection of *Calibrachoa* sp. identified as 00P108, not patented.

*Male, or pollen, parent.*—Proprietary selection of *Calibrachoa* sp. identified as 00P150, not patented.

Propagation:

*Type cutting.*—Terminal vegetative cuttings.

*Time to initiate and develop roots.*—About 18 to 20 days at 20° C.

*Time to produce a rooted young plant.*—About 20 to 28 days at 20° C.

*Root description.*—Fine, fibrous, well-branched and white in color.

*Rooting habit.*—Freely-branching.

Plant description:

*Form.*—Annual flowering plant; initially upright to semi-upright then cascading; uniform flattened mounded appearance.

*Usage.*—Appropriate for hanging baskets, window boxes and patio containers.

*Plant height* (*from soil level to top of plant plane*).—About 8 cm.

*Plant diameter* (*area of spread*).—45 to 55 cm.

*Growth rate.*—Vigorous.

*Branching habit.*—Well-branched; pinching during production is recommended.

*Stem description.*—Main branches, length: About 48 to 73 cm. Main branches, diameter: About 2.8 to 3.1 mm. Lateral branches, length: About 37 cm. Lateral branches, diameter: About 1.1 mm. Internode length: About 13 mm. Texture: Slightly pubescent, rough. Color: 146C overlain with 199A.

*Foliage description.*—Leaves simple, generally symmetrical and long persisting; sessile. Arrangement: Alternate. Length: About 2.7 to 3.4 cm. Width: About 1 to 1.2 cm. Shape: Ovate. Apex: Rounded. Base: Attenuate. Margin: Entire. Texture, upper and lower surfaces: Smooth, leathery. Venation pattern: Pinnate, only main vein is visible. Color: Immature foliage, upper surface: 146A. Immature foliage, lower surface: 146B. Fully expanded foliage, upper surface: 147A. Fully expanded foliage, lower surface: 137B. Venation, upper surface: 146A. Venation, lower surface: 136B.

Flower description:

*Flower type and habit.*—Flowers face somewhat upright or outward; single, axillary; salverform. Flowers not persistent.

*Freely flowering habit.*—Flowers not fragrant.

*Natural flowering season.*—Spring until frost in the autumn; flowering continuous during this time.

*Time to flower.*—Early flowering; plants begin flowering about 10 to 11 weeks after planting.

*Flower longevity on the plant.*—About 7 days.

*Flower size.*—Diameter: About 3.1 cm. Tube length: About 1.6 cm. Throat diameter, distal end: About 9.5 mm. Tube diameter, proximal end: About 3.7 mm.

*Flower buds.*—Length: About 2.1 cm. Diameter: About 4.5 mm. Shape: Oblong. Color: Towards the base and middle, 154D overlain with 79A; at the tip, close to 76C to 76D.

*Corolla.*—Arrangement/appearance: Single whorl of five petals, fused into flared trumpet.

*Petal length from throat.*—About 1.4 cm.

*Petal width.*—About 1.5 cm.

*Petal shape.*—Obtuse, rounded.

*Apex.*—Obtuse.

*Petal margin.*—Entire.

*Petal texture, upper and lower surfaces.*—Smooth.

*Color.*—Petal, upper surface, when opening: 81C. Petal, lower surface, when opening: 76C. Petal, upper surface, fully opened: 82C to 82D, overlain with 76A; venation, 83A. Petal, lower surface, fully opened: 76C; lateral venation 79A to 79B, main vein 77A. Circumorbital ring ("eye"), fully opened: 82A. Flower throat (inside): 9B to 9C; venation, 146C and 166A. Flower tube (outside): 1D overlain with 166A; venation, 79A to 79B.

*Sepals.*—Arrangement/appearance: Single whorl of five sepals, star-shaped. Length: About 1.4 cm. Width: About 4.3 mm. Shape: Lanceolate. Apex: Slightly rounded. Margin: Entire. Texture, upper and lower surfaces: Dull. Color: Upper and lower surfaces: 137A to 137B.

*Peduncles.*—Length: About 1.4 cm. Width: About 9 mm. Strength: Flexible, wiry. Color: 144A.

*Reproductive organs.*—Stamens: Quantity: Five per flower. Anther shape: Four-parted, ovate. Anther length: About 1.5 mm. Anther color: 12B. Pollen amount: Moderate. Pollen color: 12A to 12B. Pistils: Quantity: One per flower. Pistil length: About 8 mm. Stigma shape: Ovate. Stigma color: 144A. Style length: About 5 mm. Style color: 144C. Ovary color: 144B to 144C.

*Seed/fruit.*—Seed and fruit production has not been observed.

Disease/pest resistance: Plants of the new *Calibrachoa* have not been noted to be resistant to diseases and pests common to *Calibrachoas.*

Weather/temperature tolerance: Plants of the new *Calibrachoa* have been observed to tolerate temperatures from 2 to 30° C.

It is claimed:

1. A new and distinct cultivar of *Calibrachoa* plant named 'Wescaice', as illustrated and described.

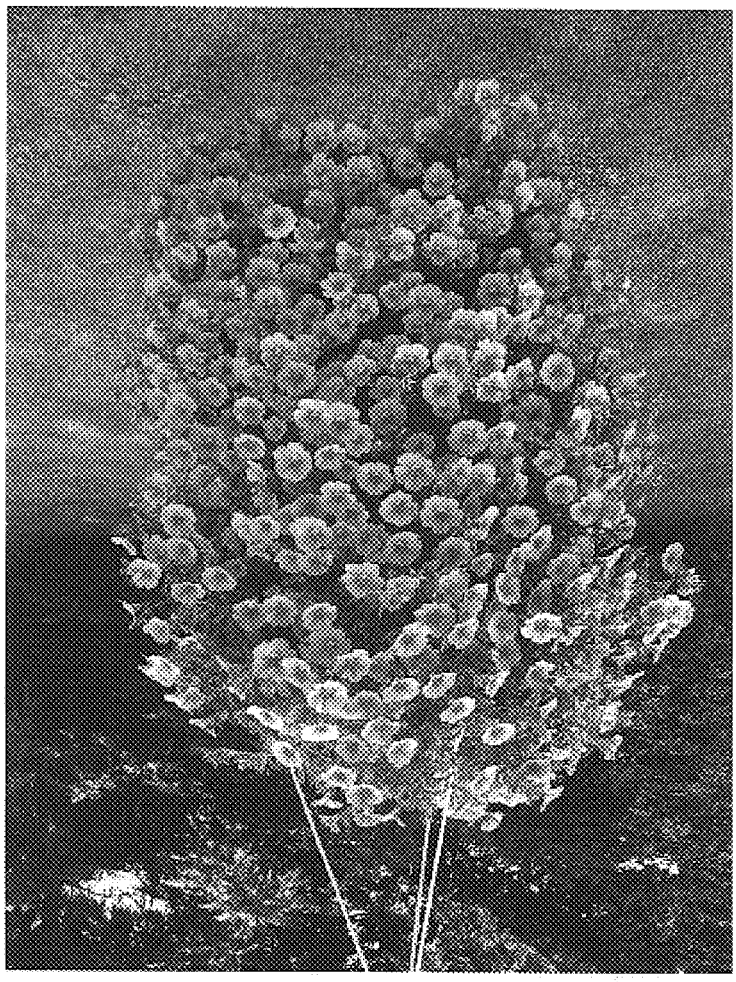
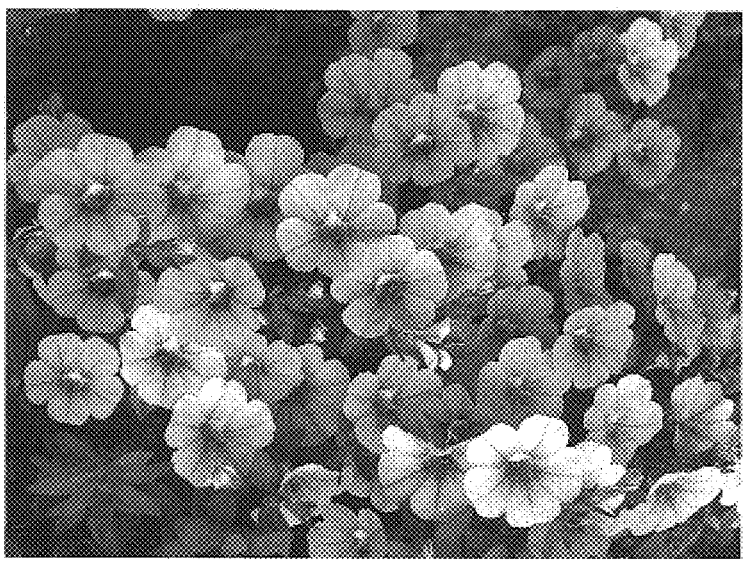

* * * * *